United States Patent
Todo (10) Patent No.: US 7,655,459 B2
(45) Date of Patent: Feb. 2, 2010

(54) ENHANCER OF ANTICANCER ACTIVITY IN VIRAL THERAPY AND METHOD OF PREVENTING OR TREATING CANCER

(76) Inventor: Tomoki Todo, 1-3-17-110, Etchujima, Koto-ku, Tokyo 135-0044 (JP)

( * ) Notice: Subject to any disclaimer, the term of this patent is extended or adjusted under 35 U.S.C. 154(b) by 118 days.

(21) Appl. No.: 10/594,964

(22) PCT Filed: Mar. 31, 2005

(86) PCT No.: PCT/JP2005/063980
§ 371 (c)(1), (2), (4) Date: Sep. 29, 2006

(87) PCT Pub. No.: WO2005/094867
PCT Pub. Date: Oct. 13, 2005

(65) Prior Publication Data
US 2007/0154451 A1    Jul. 5, 2007

(30) Foreign Application Priority Data
Mar. 31, 2004    (JP) .............................. 2004-105487

(51) Int. Cl.
C12N 15/00    (2006.01)
(52) U.S. Cl. .................................................. 435/320.1
(58) Field of Classification Search .............. 424/199.1, 424/231.1; 435/320.1, 69.1
See application file for complete search history.

(56) References Cited

U.S. PATENT DOCUMENTS

2002/0187163 A1    12/2002 Johnson et al.
2003/0091537 A1*    5/2003 Coffin .................. 424/93.2

FOREIGN PATENT DOCUMENTS

JP    2001-513508    9/2001
WO    WO 02/076216 A1    10/2002

OTHER PUBLICATIONS

Yamanaka et al, Cancer Immunol. Immunother. 1999, 48(6):297-302.*
Hara et al, Cancer Gene Therapy, 2000, vol. 7, pp. 83-90.*
Bennett et al, Annals of Surgery, 2001, vol. 233, No. 6, pp. 819-826.*
Partial translation of: Seikagaku Jien (3rd Edition), Kabushiki Kaisha Tokyo Kagaku Dojin, 1998, p. 156, right column.
Martuza, et al.; Experimental Therapy of Human Glioma by Means of a Genetically Engineered Virus Mutant; May 10, 1991; Science, vol. 252; pp. 854-856.
Chahlavi, et al.; Replication—Competent Herpes Simplex Virus Vector G207 and Cisplatin Combination Therapy for Head and Neck Squamous Cell Carcinoma; Neoplasia, vol. 1, No. 2; Jun. 1999; pp. 162-169.
Hunter, et al.; Attenuated, Replication—Competent Herpes Simplex Virus Type 1 Mutant G207: Safety Evaluation of Intracerebral Injection in Nonhuman Primates; Journal of Virology, vol. 73, No. 8, Aug. 1999; pp. 6319-6326.
Chahlavi, et al.; Effect of Prior Exposure to Herpes Simplex Virus 1 on Viral Vector—Medicated Tumor Therapy in Immunocompetent Mice; Gene Theraphy, vol. 6, 1999, pp. 1751-1758.
Nakamura, et al.; Glial Expression of Fibroblast Growth Factor-9 in Rat Central Nervous System; GLIA 28; 1999, pp. 53-65.
Todo, et al.; Systemic Antitumor Immunity in Experimental Brain Tumor Therapy Using a Multimutated, replication—Competent Herpes Simplex Virus; Human Gene Therapy, vol. 10; Nov. 20, 1999; pp. 2741-2755.
Todo, e al.; Corticosteroid Adminstration Does not Affect Viral Oncolytic Activity, but Inhibits Antihumor Immunty in Replication Competent Herpes Simplex Virus Tumor Therapy; Human Gene Theraphy vol. 10; Nov. 20, 1999; pp. 2869-2878.
Todo, et al.; Evaluation of Ganciclovir—Mediated Enhancement of the Antitumoral Effect in Oncolytic, Multimutated Herpes Simplex Virus Type 1(G207) Therapy of Brain Tumors; Cancer General Theraphy, vol. 7, No. 6, 2000; pp. 939-946.
Merkert, et al.; Conditionally replicating Herpes Simplex Virus Mutant, G207 for the treatment of malignant Glioma: results of phase 1 Trial; Gene Theraphy, vol. 7; 2000; pp. 867-874.
Toda, et al.; Viral Shedding and Biodistribution of G207, a Mulitmutated, Conditionally Replicating Herpes Simples Virus Type 1, After Intracerebral Inoculation in Aotus; Molecular Therapy, vol. 2, No. 6, pp. 588-595.

(Continued)

Primary Examiner—Ali R. Salimi
(74) Attorney, Agent, or Firm—Morgan Lewis & Bockius LLP (57) ABSTRACT

The present invention provides a pharmaceutical that safely and effectively enhances the anticancer activity of viral therapy and particularly the antitumor immunity of viral therapy. The present invention also provides a method of preventing or treating cancer that uses this drug. The anticancer activity enhancer according to the present invention contains interleukin as an effective component and is co-administered with a recombinant herpes simplex virus that selectively replicates in cancer cells.

12 Claims, 9 Drawing Sheets

OTHER PUBLICATIONS

Nakano, et al.; Theraputic Efficacy of G207, a Conditionally Replicating herpes Simplex Virus Type 1 Mutant, for Gallbladder Carcinoma in Immunocompetent Hamsters; Molecular Therapy vol. 3, No. 4, Apr. 2001.

Varghese, et al., Preclinical Safety Evaluation of G207, a Replication Competent Herpes Simplex Virus Type 1, Inoculated Intraprostatically in Mice and Nonhuman Primates; Human Gene Therapy vol. 12; May 20, 2001; pp. 999-1010.

Jorgensen, et al.; Ionizing Radiation Does Not Alter the Antitumor Activity of Herpes Simplex Virus Vector G207 in Subcutaneous Tumor Models of Human and Murine Prostate Cancer; Neoplasia, vol. 3, No. 5; 2001; pp. 451-456.

Todo, et al.; Oncolytic Herpes Simplex Virus (G207) Therapy From Basic to Clinical; Tumor Supressing Viruses, Genes, and Drugs—Inovative Cancer Therapy Approaches; 2001; pp. 45-75.

Todo, et al.; Oncolytic Herpes Simplex Virus Vector With Enhanced MHC Class 1 presentation and Tumor Cel Killing; Pro. Natl. Acad. Sci. USA, 2001, vol. 92, pp. 6396-6401.

Todo, et al.; Herpes Simples Virus as an in Situ Cancer Vaccine for the Induction of Specific Anti-Tumor Immunity; Human Gene Therpy 10, Feb. 10, 1999; pp. 385-393.

Todo, et al.; In Situ Expression of Soluble B7-a in the Context of Oncolytic Herpes Simplex Virus Induces Potent Antitumor Immunity; Cancer Research, vol. 61; Jan. 1, 2001, pp. 153-161.

Katsanis, et al.; B7-1 Expression decreases tumorigenicity and induces partial systemic immunity to murine neuroblastoma deficient in major histocompatibilty complex and costimulatory molecules; Cancer Gene Therapy, vol. 2, No. 1, 1995; pp. 39-46.

Katsanis, et al.; Irradiation of Singly and Doubly Transduced Murine Neuroblastoma Cells Expressing B7-1 and Producing Interferon-Gamma Reduces their Capacity to induce Systemic Immunity; Cancer Gene Therapy, vol. 3, No. 2, 1996; pp. 75-82.

Heuer, et al.; Retrovirus-mediated Gene Transfer of B7-1 and MHC Class II Converts a Poorly Immunogenic Neuroblastoma into a Highly Immunogenic One; Human Gene Therapy, vol. 7, Nov. 10, 1996; pp. 2059-5068.

Seikagaku Jien (3rd Edition), Kabushiki Kaisha Tokyo Kagaku Dojin, 1998, p. 156, right column.

Varghese, et al.; Oncolytic Herpes Simplex Virus vectors for cancer Virotherapy; Cancer Gene Therapy, vol. 9, 2002; pp. 967-978.

Coughlin et al. Interleukin-12 and Interleukin-18 Synergistically Induce Murine Tumor Regression which Involves Inhibition of Angiogenesis. J. Clin. Invest: 101(6):144-1452 (1998).

Ino et al. Triple Combination of Oncolytic Herpes Simplex Virus-1 Vectors Armed with Interleukin-12, Interleukin-18, or soluble B7-1 results in Enhanced Antitumor Efficacy. Clin. Cancer Research 12:643-652 (2006).

Toda et al. In Situ Cancer Vaccination: An IL-12 Defective Vector/Replication-Competent Herpes Simplex Virus Combination Induces Local and Systemic Antitumor Activity. J. Immunol. 160:4474-4464 (1998).

* cited by examiner

ENHANCER OF ANTICANCER ACTIVITY IN VIRAL THERAPY AND METHOD OF PREVENTING OR TREATING CANCER

The present application is a U.S. National Phase application of International Application PCT/JP2005/006398, filed Mar. 31, 2005, which claims the benefit of J.P. Application 2004-105487, filed Mar. 31, 2004, which is incorporated by reference in its entirety.

BACKGROUND

The present invention relates to an enhancer of anticancer activity in viral therapy, which contains interleukin as an effective component. The present invention further relates to a method of preventing or treating cancer in which interleukin is co-administered with recombinant herpes simplex virus.

Based on knowledge of the cytomolecular mechanisms of viral infection, the genetic mechanisms related to carcinogenesis, and the molecular biological mechanisms underlying cancer cell proliferation, viruses that selectively replicate in cancer cells have been produced in recent years by viral genome modification using genetic engineering techniques, and efforts are being made to apply these viruses to the treatment of cancer.

The concept of the application of recombinant viruses to the treatment of cancer was proposed by Martuza et al., in 1991 (see, for example, Martuza, R. L. et al., Science 252: 854-6 (1991)). Many viruses are themselves pathogenic and also have a negative effect on normal cells when administered unattenuated to, for example, humans. However, through the deletion of specific genes by genetic recombination, viruses can be constructed which are incapable of synthesizing viral DNA in normal cells and hence are incapable of replicating in normal cells, but which are capable of replicating in proliferating tumor cells due to a compensation therein for the function of the deleted genes.

Oncolytic viruses, which have been modified by genetic recombination to selectively replicate only within cancer cells, replicate in situ when infected into cancer cells and by this process cause the destruction of the host cancer cells. The replicated virus then spreads into the surroundings and again infects cancer cells, thereafter showing an antitumor activity by repetition of the steps of replication, cell death, spread, and infection. Therapeutic virus that has infected normal cells, on the other hand, is incapable of replicating and as a result does not damage normal tissue.

An example of such a mutant virus is the dlsptk mutant virus, which is constructed by deletion of the thymidine kinase (tk) gene from the genome of herpes simplex virus type 1 (HSV-1). Dlsptk is unable to synthesize viral DNA in normal cells and thus is unable to replicate in normal cells; however, the high tk activity of proliferating tumor cells compensates for the lost viral tk and the virus is then able to replicate. It has been shown in animal brain tumor models that infection of tumor cells with dlsptk results in the appearance of a therapeutic effect through selective rupture of only tumor cells (see, for example, Martuza, R. L. et al., Science 252: 854-6 (1991)).

HSV-1 is classified as an enveloped double-stranded DNA virus and has the following characteristics that are advantageous for the treatment of cancer: 1) it can infect many types of human cells; 2) the life cycle and genomic sequence of this virus have been elucidated; 3) for most of the genes of this virus, the function is known and genetic manipulation can be applied; and 4) the large size of the viral genome (about 152 kb) makes it possible to integrate large genes or multiple numbers of genes. HSV-1 also has the following advantages in terms of clinical application: 5) death of the entire tumor cell population is possible at a low multiplicity of infection (MOI); 6) anti-viral drugs that inhibit viral replication are available; 7) anti-HSV-1 antibodies in the blood do not affect the cell-to-cell spread of infection by the virus; 8) since mice and non-human primates sensitive to HSV-1 are available, pre-clinical evaluation of safety and efficacy can be carried out in animals; and 9) the viral DNA does not integrate into the genome of the host cell and stays episomal.

Within the sphere of oncolytic viruses, to date the present inventor has played an important role in the development of G207, a γ34.5 gene-deleted HSV-1 with an inactivated ICP6 gene (for example, refer to Chahlavi, A. et al., Neoplasia 1: 162-169 (1999); Hunter, W. D. et al., J. Virol. 73: 6319-6326 (1999); Chahlavi, A. et al., Gene Ther. 6: 1751-1758 (1999); Nakamura, S. et al., Glia 28: 53-65 (1999); Todo, T. et al., Hum. Gene Ther. 10: 2741-2755 (1999); Todo, T. et al., Hum. Gene Ther 10: 2869-2878 (1999); Todo, T. et al., Cancer Gene Ther. 7: 939-946 (2000); Markert, J. M. et al., Gene Ther. 7: 867-874 (2000); Todo, T. et al., Mol. Ther. 2: 588-595 (2000); Nakano, K. et al., Mol. Ther. 3: 431-437 (2001); Varghese, S. et al., Hum. Gene Ther. 12: 999-1010 (2001); Jorgensen, T. J. et al., Neoplasia 3: 451-456 (2001); and Todo, T. et al., San Diego, Academic Press: 45-75 (2001)), and has also invented and developed G47Δ, an HSV-1 in which, in addition to the two genes already mentioned, the ICP47 gene (also known as the α47 gene) is also inactivated (refer, for example, to US Published Application 2002/0187163A1; Todo, T. et al., Proc. Natl. Acad. Sci. USA 98: 6396-6401 (2001)). G207 and G47Δ, while having lost the ability to replicate in normal tissue, retain the ability to replicate in tumor cells. Due to the modification of three genes therein, G47Δ in particular is very useful as a therapeutic virus that exhibits a high tumor specificity and high safety.

Furthermore, in investigations using mice with normal immune systems, the present inventor found that genetically recombinant HSV-1, upon intratumoral inoculation, not only proliferated within the tumor, thereby exhibiting a cell-killing activity, but also elicited a specific antitumor immunity, thereby enhancing its antitumor activity (refer to, for example, Todo, T. et al., Hum. Gene Ther. 10: 2741-2755 (1999); Todo, T. et al., Hum. Gene Ther. 10: 2869-2878 (1999); and Toda M. et al., Hum. Gene Ther. 10: 385-393 (1999)). For example, when G207 was intratumorally inoculated into N18 tumors (neuroblastoma) generated subcutaneously in A/J mice, a systemic antitumor immunity was induced associated with an elevation of activity by cytotoxic T lymphocytes (CTLs) specific to N18 cells, and the growth of remote subcutaneous or intracerebral tumors was also inhibited. Mice cured by treatment with G207 acquired a tumor-specific protective immunity, and the elevation in N18 cell-specific CTL activity persisted for more than a year. In other words, the intratumoral inoculation of oncolytic HSV-1 also functions as an in situ cancer vaccine, which is extremely advantageous from a clinical standpoint for the following reasons: identification of a tumor antigen is not required; greater convenience as compared to the ex vivo method that requires, inter alia, tumor cell culture; and the possibility that treatment of the primary focus will also be able to suppress metastatic foci through a systemic antitumor immunity.

SUMMARY

In cancer treatment using a recombinant herpes simplex virus (referred to below simply as recombinant HSV) such as G207, the introduction of a sufficient quantity of virus into the tumor tissue is one prerequisite for the manifestation of its effect. However, this ideal circumstance is not necessarily always realized clinically.

A method and/or drug that could enhance the anticancer activity of recombinant HSV without producing side effects would make viral treatment more useful. In addition, if, among the anticancer activities provided by viral therapy, the antitumor immunity in particular could be enhanced, then the appearance of an anticancer activity could be expected even at locations outside the cancer tissue inoculated with the virus and a higher therapeutic effect could be expected even at metastatic foci.

An object of the present invention, therefore, is to provide a drug that safely and effectively enhances the anticancer activity of viral therapy and in particular that safely and effectively enhances the antitumor immune response in viral therapy. Another object of the present invention is to provide a method of preventing or treating cancer that uses this drug.

The present inventor carried out extensive and intensive research in view of the circumstances cited above and as a result discovered that, when recombinant HSV that selectively proliferates in cancer cells is administered as a cancer therapy, the therapeutic effect can be enhanced by the co-administration of interleukin 18 (abbreviated hereafter as IL-18) and this effect can be obtained to a satisfactory degree even at locations outside the cancer tissue that received the HSV inoculation. It was also discovered that when interleukin 18 is administered systemically, its effect can be enhanced still further by the administration or expression of interleukin 12 at the site of the tumor. The present invention was achieved based on these discoveries.

That is, the present invention relates to

[1] an enhancer of the anticancer activity in viral therapy, having interleukin as an effective component, wherein the enhancer is administered systemically and is used in combination with a recombinant herpes simplex virus that selectively replicates in cancer cells;

[2] the enhancer according to [1], wherein the interleukin is interleukin 18;

[3] the enhancer according to [1] or [2], wherein the anticancer activity comprises eliciting antitumor immunity;

[4] the enhancer according to any of [1] to [3], wherein the γ34.5 gene and ICP6 gene of the recombinant herpes simplex virus have been deleted or inactivated;

[5] the enhancer according to [4], wherein the ICP47 gene of the recombinant herpes simplex virus has also been deleted or inactivated;

[6] the enhancer according to any of [1] to [5], wherein a gene coding for interleukin 12 has been inserted as an expressible construct in the genomic DNA of the recombinant herpes simplex virus;

[7] a method of preventing or treating cancer, comprising the co-administration of interleukin and a recombinant herpes simplex virus that selectively replicates in cancer cells;

[8] the method according to [7], wherein the interleukin is interleukin 18;

[9] the method according to [7] or [8], wherein the interleukin 18 is administered systemically;

[10] the method according to [9], wherein interleukin 12 is additionally administered locally at a tumor tissue;

[11] the method according to [9], wherein a gene coding for interleukin 12 has been inserted as an expressible construct in the genomic DNA of the recombinant herpes simplex virus;

[12] the method according to any of [7] to [11], wherein the γ34.5 gene and ICP6 gene of the recombinant herpes simplex virus have been deleted or inactivated;

[13] the method according to [12], wherein the ICP47 gene of the recombinant herpes simplex virus has also been deleted or inactivated;

[14] the method according to any of [7] to [13], wherein the method of preventing or treating cancer is a method of preventing or treating cancer at a location outside the tumor tissue inoculated with the recombinant herpes simplex virus;

[15] an agent for treating or preventing cancer, wherein the agent contains recombinant herpes simplex virus that selectively replicates in cancer cells and the agent is administered by injection within a tumor tissue in combination with the systemic administration of interleukin 18, and wherein the γ34.5 gene and ICP6 gene of the recombinant herpes simplex virus have been deleted or inactivated and a gene coding for interleukin 12 has been inserted as an expressible construct in the genomic DNA of the recombinant herpes simplex virus; and

[16] the agent according to [15] for treating or preventing cancer, wherein the ICP47 gene of the recombinant herpes simplex virus has also been deleted or inactivated.

The present invention can substantially raise the efficacy of viral therapy by the co-administration of recombinant herpes simplex virus that selectively replicates in cancer cells and an enhancer of anticancer activity that contains interleukin, and particularly IL-18, in a dose low enough to lack toxicity. In addition, when the IL-18 is administered systemically, an additional enhancement in this efficacy can be obtained by the administration of IL-12 at the site of the tumor. The co-administration of these interleukins in particular enhances the antitumor immunity elicited by viral therapy and thereby also raises the therapeutic effect at locations outside the tumor tissue that has been inoculated with the virus. Since this indicates that the method according to the present invention is also effective at metastatic foci generated at a plurality of sites, the method according to the present invention raises the usefulness of viral therapy to another level.

DETAILED DESCRIPTION

The meaning of the terms and so forth used by the present invention is made clear in the following, and the present invention is also described in detail herebelow.

The "viral therapy" cited by the present invention refers to a therapy that cures cancer through the administration of a virus that selectively replicates in cancer cells and that is unable to replicate in normal cells, thereby destructing only cancer cells. The virus is provided with this selective replication capacity by modification by genetic engineering techniques or by natural mutation, or has this property natively.

The virus used in the viral therapy according to the present invention can be exemplified by recombinant HSV that has been modified to selectively replicate in cancer cells and by naturally mutated herpes simplex virus that selectively replicates in cancer cells. Such a virus can be, for example, HSV in which the γ34.5 gene and ICP6 gene have been deleted or inactivated and HSV in which the ICP47 gene has also been deleted or inactivated.

The γ34.5 gene product is a protein which antagonizes the function of double-stranded RNA-activated protein kinase (PKR). In normal cells, PKR is phosphorylated in response to HSV-1 infection, and this phosphorylates translation initiation factor eIF-2α, resulting in inhibition of viral protein synthesis. Thus, virus replication is inhibited in normal cells if γ34.5 gene does not function. However, in cancer cells, and particularly in cells in which the Ras signal transduction pathway has been activated, since PKR is already inhibited, virus replication is possible even in mutant HSV-1 in which γ34.5 has been deleted.

ICP6 gene is a gene which encodes a large subunit of ribonucleotide reductase (RR). If the RR gene is removed or inactivated, HSV-1 cannot replicate in non-dividing cells (normal cells). However, replication is possible in actively dividing cells in which RR activity is increased by compensating for the missing virus enzyme.

ICP47 protein decreases the expression of MHC class I of infected cells by inhibiting transporter associated with antigen processing (TAP), and acts so as to allow the virus to escape the host's immunosurveillance. Consequently, antitumor immunity is enhanced if ICP47 gene is inactivated since the expression of MHC class I is maintained in infected cancer cells.

The G207 cited above is an example of HSV in which the γ34.5 gene and ICP6 gene have been deleted or inactivated, and the G47Δ cited above is an example of HSV in which three genes, γ34.5, ICP6, and ICP47, have been deleted or inactivated. G47Δ is the better adapted for viral therapy because its triple mutation results in high safety and highly tumor-specific replication.

These recombinant HSVs can be suitably constructed by the individual skilled in the art by the methods described in the literature cited above or by methods based thereon.

The enhancer according to the present invention of the anticancer activity in viral therapy contains interleukin as an effective component. Interleukin refers to a family of bioactive proteins that are produced by immunocompetent cells such as lymphocytes, monocytes, and macrophages, and 29 species, from IL-1 to IL-29, are known at present. There are no particular limitations on the interleukin comprised in the anticancer activity enhancer according to the present invention as long as the interleukin, when used in combination with viral therapy, is able to enhance the anticancer activity thereof; preferred, however, are IL-12, which is a natural killer cell-stimulating factor, IL-18, which has been cloned as a cytokine synthesized by Kupffer cells, IL-23, which has the same p40 subunit as IL-12 and was discovered as a factor that strongly induces the proliferation of memory T-lymphocytes (Cordoba-Rodriguez, R.; *Expert Opin. BioL Ther.* 2003 August: 3(5) 715-23), IL-27 (Cordoba-Rodriguez, R.; *Expert Opin. Biol. Ther.* 2003 August: 3(5) 715-23), and so forth, wherein IL-18 and IL-12 are well suited thereamong.

IL-18 is an inflammatory cytokine with a molecular weight of 18,000 that is known as interferon γ-inducing factor (IGIF). IL-18 is known to have, inter alia, the following biological activities: inducing the production of interferon γ (referred to below as IFN-γ) by T cells and NK cells, enhancing the activity of NK cells, enhancing the expression of the Fas ligand by lymphocytes, and inducing the production of granulocyte-macrophage colony-stimulating factor.

While it has also been reported that the interleukins by themselves exhibit anticancer activity, they must be administered at high concentrations in order to obtain satisfactory results, and their utility is therefore also limited from the standpoint of side effects. When, however, they are used in combination with recombinant HSV as the anticancer activity enhancer according to the present invention, an anticancer activity substantially higher than that for the use of the virus alone can be obtained by the administration of interleukin at a dose low enough to lack toxicity.

Furthermore, it has been discovered that the systemic administration of IL-18 according to the present invention also provides a large increase in the anticancer activity at locations outside the tumor tissue inoculated with the virus. This shows that IL-18, among the anticancer activities exercised by viral therapy, contributes in particular to strengthening the antitumor immunity and that the anticancer activity enhanced according to the present invention is also useful for cancer patients in which cancer has appeared at multiple locations and cancer patients having metastatic foci.

It has also been discovered that the aforementioned effects due to the systemic administration of IL-18 in the present invention are further enhanced by the local administration of IL-12 at the tumor tissue. In general, although an anticancer activity is shown when IL-18 and IL-12 are systemically administered, strong side effects are frequently seen as well. However, the anticancer activity due to the co-use of recombinant HSV and IL-18 in the method according to the present invention can be enhanced by the local administration of IL-12, while the appearance of side effects can be suppressed. There are no particular limitations on the procedure for the local administration of IL-12, and, for example, a procedure can be used in which a gene encoding IL-12 is expressibly inserted in the genomic DNA of the recombinant HSV used by the present invention and this recombinant HSV is then administered. When this procedure is employed, the recombinant HSV may be inoculated only at the tumor tissue by injection or may be systemically administered by, for example, intravenous administration. Since the recombinant HSV used by the present invention selectively proliferates in cancer cells, IL-12 is still expressed primarily in tumor cells even in the case of systemic administration. In the case of the direct administration of IL-12 protein separately from recombinant HSV, local administration may be carried out by, for example, injection at the tumor tissue.

The expressible insertion of a gene encoding IL-12 in the genomic DNA of the recombinant HSV denotes the insertion of this gene in the genomic DNA of the recombinant HSV in a state in which the gene is functionally linked downstream from a promoter. "Functionally linked" refers to a linkage between a promoter and the IL-12 gene that enables initiation of transcription of the IL-12 gene positioned downstream from the promoter upon the binding of transcription factors to the promoter. The promoter may be a promoter natively present in the genomic DNA of HSV or may be inserted into the genomic DNA of the HSV in the form of an expression cassette that includes the IL-12 gene.

The interleukin comprised in the anticancer activity enhancer according to the present invention may be of biological origin or may be produced by genetic engineering techniques. The treatment of humans is most preferably carried out using human interleukin.

The mode of administration of the anticancer activity enhancer according to the present invention is not particularly limited, and oral and non-oral routes may be used. The dosage in the case of mammals (for example, humans, mice, rats, guinea pigs, rabbits, dogs, horses, primates, and so forth) and particularly in the case of administration to humans cannot be specifically limited since it varies as a function of the severity of the disease, the age, gender, and weight of the patient, differences in sensitivity, the method of administration, the period of administration, the interval between administrations, the properties, composition, and type of the drug formulation, the type of effective component, and so forth. However, administration can be carried out so as to provide an amount of the interleukin effective component of about 2 μg to about 5 g, preferably about 20 μg to about 500 mg, and more preferably about 100 μg to about 25 mg, or in the case of administration by injection about 0.03 to 3000 μg/kg and preferably 0.1 to 1000 μg/kg. In each case administration can be carried out a single time or can be carried out divided into several administrations.

The subject anticancer activity enhancer according to the present invention can be formulated by conventional methods by mixing the interleukin with, for example, a pharmaceutically acceptable carrier known as such. The dosage form is not particularly limited and can be exemplified by tablets, powders, fine granules, granules, coated tablets, capsules, syrups, troches, inhalants, suppositories, injectables, ointments, ophthalmic ointments, ophthalmic solutions, nose drops, ear drops, poultices, and lotions, wherein an injectable is particularly preferred. In order to prepare the formulation, use can be made of the usual excipients, binders, disintegrants, lubricants, colorants, flavor-masking/odor-masking agents, and as necessary stabilizers, emulsifying agents, absorption promoters, surfactants, pH regulators, preservatives, antioxidants, and so forth. The formulation can be prepared by the usual methods by blending the components used in the form of the usual raw materials for drug formulation.

Examples are plant and animal oils such as soybean oil, beef tallow, synthetic glycerides, and so forth; hydrocarbons such as liquid paraffin, squalane, solid paraffin, and so forth; ester oils such as octyldodecyl myristate, isopropyl myristate, and so forth; higher alcohols such as cetostearyl alcohol, behenyl alcohol, and so forth; silicone resins; silicone oils; surfactants such as polyoxyethylene fatty acid esters, sorbitan fatty acid esters, glycerol fatty acid esters, polyoxyethylene sorbitan fatty acid esters, polyoxyethylene hydrogenated castor oil, polyoxyethylene-polyoxypropylene block copolymers, and so forth; water-soluble polymers such as hydroxyethyl cellulose, polyacrylic acid, carboxyvinyl polymers, polyethylene glycol, polyvinylpyrrolidone, methyl cellulose, and so forth; lower alcohols such as ethanol, isopropanol, and so forth; polyhydric alcohols such as glycerol, propylene glycol, dipropylene glycol, sorbitol, and so forth; sugars such as glucose, sucrose, and so forth; inorganic powders of, for example, silicic anhydride, aluminum magnesium silicate, aluminum silicate, and so forth; and purified water. The excipient can be exemplified by lactose, corn starch, sucrose, glucose, mannitol, sorbitol, crystalline cellulose, silicon dioxide, and so forth. The binder can be exemplified by polyvinyl alcohol, polyvinyl ether, methyl cellulose, ethyl cellulose, gum arabic, tragacanth, gelatin, shellac, hydroxypropyl cellulose, hydroxypropyl methyl cellulose, polyvinylpyrrolidone, polypropylene glycol polyoxyethylene block polymer, meglumine, calcium citrate, dextrin, pectin, and so forth. The disintegrant can be exemplified by starch, agar, gelatin powder, crystalline cellulose, calcium carbonate, sodium bicarbonate, calcium citrate, dextrin, pectin, calcium carboxymethyl cellulose, and so forth. The lubricant can be exemplified by magnesium stearate, talc, polyethylene glycol, silica, hydrogenated plant oils, and so forth. The colorant can be exemplified by any colorant allowed for addition to drugs. The taste-masking/odor-masking agent can be exemplified by cocoa powder, menthol, aromatic powder, peppermint oil, borneol, cinnamon powder, and so forth. The antioxidant can be exemplified by antioxidants acceptable for addition to drugs, such as ascorbic acid, α-tocopherol, and so forth.

The oral formulation, for example, a powder, fine granule, granule, tablet, coated tablet, capsule, and so forth, can be prepared by the usual methods after the addition of excipient and optionally binder, disintegrant, lubricant, colorant, taste-masking/odor-masking agent, and so forth.

As necessary, a tablet or granule may be suitably coated with a sugar coating, gelatin coating, or other coating.

A solution, such as a syrup, injectable formulation, ophthalmic solution, and so forth, can be formulated by the usual methods by the addition of a pH regulator, solvent, tonicity agent, and so forth, and optionally by the addition of solubilizing agent, stabilizer, buffer, suspending agent, antioxidant, and so forth. These solutions can also be made into freeze-dried materials. An injectable formulation can be administered intravenously, subcutaneously, or intramuscularly. Suitable examples of the suspending agent are methyl cellulose, polysorbitol 80, hydroxyethyl cellulose, gum arabic, tragacanth powder, sodium carboxymethyl cellulose, polyoxyethylene sorbitan monolaurate, and so forth; suitable examples of the solubilizer are polyoxyethylene hydrogenated castor oil, polysorbitol 80, nicotinamide, polyoxyethylene sorbitan monolaurate, and so forth; suitable examples of the stabilizer are sodium sulfite, sodium metasulfite, ether, and so forth; and suitable examples of the preservative are methyl para-hydroxybenzoate, ethyl para-hydroxybenzoate, sorbic acid, phenol, cresol, chlorocresol, and so forth.

The drug composition as described in the preceding is useful for the prevention or treatment of various types of cancers. Viral therapy using recombinant HSV is already known to be effective with a wide variety of solid cancers (refer to, for example, Todo, T. et al., San Diego, Academic Press: 45-75 (2001)), and the drug composition according to the present invention can be used with all of these cancers. Specific disease examples are brain tumors, head and neck cancers, esophageal cancer, stomach cancer, colon cancer, liver cancer, pancreatic cancer, lung cancer, breast cancer, skin cancer, ovarian cancer, prostate cancer, kidney cancer, bladder cancer, melanoma, neuroblastoma, and so forth. Among these, it is useful for brain tumors and neuroblastoma.

The anticancer activity enhancer according to the present invention is characteristically co-administered with a recombinant herpes simplex virus that selectively replicates in cancer cells. "Co-administration" in the present invention denotes a regime of administration that yields a synergistic effect through co-use, but is not otherwise particularly limited as to dose, method of administration, interval of administration, and so forth, and an appropriate selection can be made in accordance with the goal of the therapy, the disease, and the target of administration. For example, the recombinant HSV and anticancer activity enhancer may be administered at the same time, or either may be administered in advance of the other. Moreover, either the recombinant HSV or the anticancer activity enhancer may be administered repeatedly, or both the recombinant HSV and the anticancer activity enhancer can be administered repeatedly, and their frequencies of administration may be different. In a preferred embodiment, the anticancer activity enhancer is administered repeatedly, and during this interval the recombinant HSV is administered less frequently.

The method of administering the recombinant HSV is not particularly limited, and the recombinant HSV may be administered as such or may be formulated by conventional methods with the admixture of pharmaceutically acceptable carriers, stabilizers, emulsifying agents, and so forth that are known as such. The dosage form is not particularly limited and can be exemplified by capsules, syrups, inhalants, injectables, ointments, ophthalmic ointments, ophthalmic solutions, nose drops, ear drops, lotions, and so forth, wherein an injectable is particularly preferred.

The present invention also provides a method for preventing or treating cancer, wherein interleukin is co-administered with a recombinant herpes simplex virus that selectively replicates in cancer cells. The concepts of "recombinant herpes simplex virus that selectively replicates in cancer cells", "interleukin", "co-administration", and "cancer" are all defined here just as for the anticancer activity enhancer described in the preceding and therefore will not be explained again.

Among the interleukins, the method according to the present invention for preventing or treating cancer preferably uses IL-18. IL-18 is again defined here just as for the anticancer activity enhancer described in the preceding and therefore will not be explained again.

The recombinant HSV is preferably administered by injection into the tumor tissue in the subject method according to the present invention for preventing or treating cancer. Injection into the tumor tissue can provide a high cell-killing activity with respect to the cancer cells within this tissue. The method of administration is in accordance with that described in the preceding.

On the other hand, the interleukin, and particularly IL-18, is preferably administered systemically, and in the case of humans, for example, can be administered systemically by intravenous injection or intravenous drip. Systemic administration makes possible an enhancement of the HSV-induced antitumor immunity even outside the location of virus inoculation. The method of administering the interleukin is not particularly limited and the interleukin can be administered as such or can be administered after formulation by a conventional method by admixture with, for example, a pharmaceutically acceptable carrier known as such. The formulation methodology is in accordance with that already described and will not be described again here.

The agent according to the present invention for treating cancer and the agent according to the present invention for preventing cancer contain recombinant HSV that selectively replicates in cancer cells and are used in combination with the systemic administration of IL-18, wherein the γ34.5 gene and ICP6 gene of the recombinant HSV have been deleted or inactivated and a gene encoding IL-12 is inserted as an expressible construct in the genomic DNA thereof. Such a recombinant HSV can be constructed by inserting a gene encoding IL-12 as an expressible construct in the G207 viral genome described above. This agent for treating cancer and agent for preventing cancer have a concentration and quantity of HSV effective component that have been optimized on the assumption of co-administration with IL-18. Even when the agent according to the present invention for treating cancer or the agent according to the present invention for preventing cancer is administered systemically, it makes possible the secretion of IL-12 primarily in cancer cells because it contains recombinant HSV that selectively replicates in cancer cells.

The recombinant HSV present in the agent according to the present invention for treating cancer and in the agent according to the present invention for preventing cancer preferably also has a deleted or inactivated ICP47 gene. Such a recombinant HSV can be constructed by inserting a gene encoding IL-12 as an expressible construct in the G47Δ viral genome described above, thereby providing an even safer recombinant HSV through the deletion or inactivation of the ICP47 gene.

The reference, working, and test examples of the present invention that are given below are exemplary in nature, and the present invention is not limited to the specific examples provided hereafter. The individual skilled in the art can execute the present invention to the fullest degree by the addition of various modifications to the examples provided hereafter, and such modifications are encompassed in the scope of the patent claims of this application.

Example 1

Results of the Co-administration of IL-18 and G47Δ

The mouse neuroblastoma cell line Neuro2a was transplanted subcutaneously ($5 \times 10^6$) into A/J mice and this was used as the mouse tumor model. Neuro2a is sensitive to HSV infection and is poorly immunogenic in A/J mice. Accordingly, this model was considered to be a model in which antitumor activity caused by antitumor immunity would be the most difficult to realize. If efficacy could be shown in this model, efficacy for other cancers could also be presumed (Todo, T. et al., *Cancer Res.* 61: 153-161 (2001); Katsanis, E. et al., *Cancer Gene Ther.*, 2: 3946 (1995); Katsanis, E. et al., *Cancer Gene Ther.*, 3: 75-82 (1996); Heuer, J. G. et al., *Hum. Gene Ther.*, 7: 2059-2068 (1996)).

Figure 1:
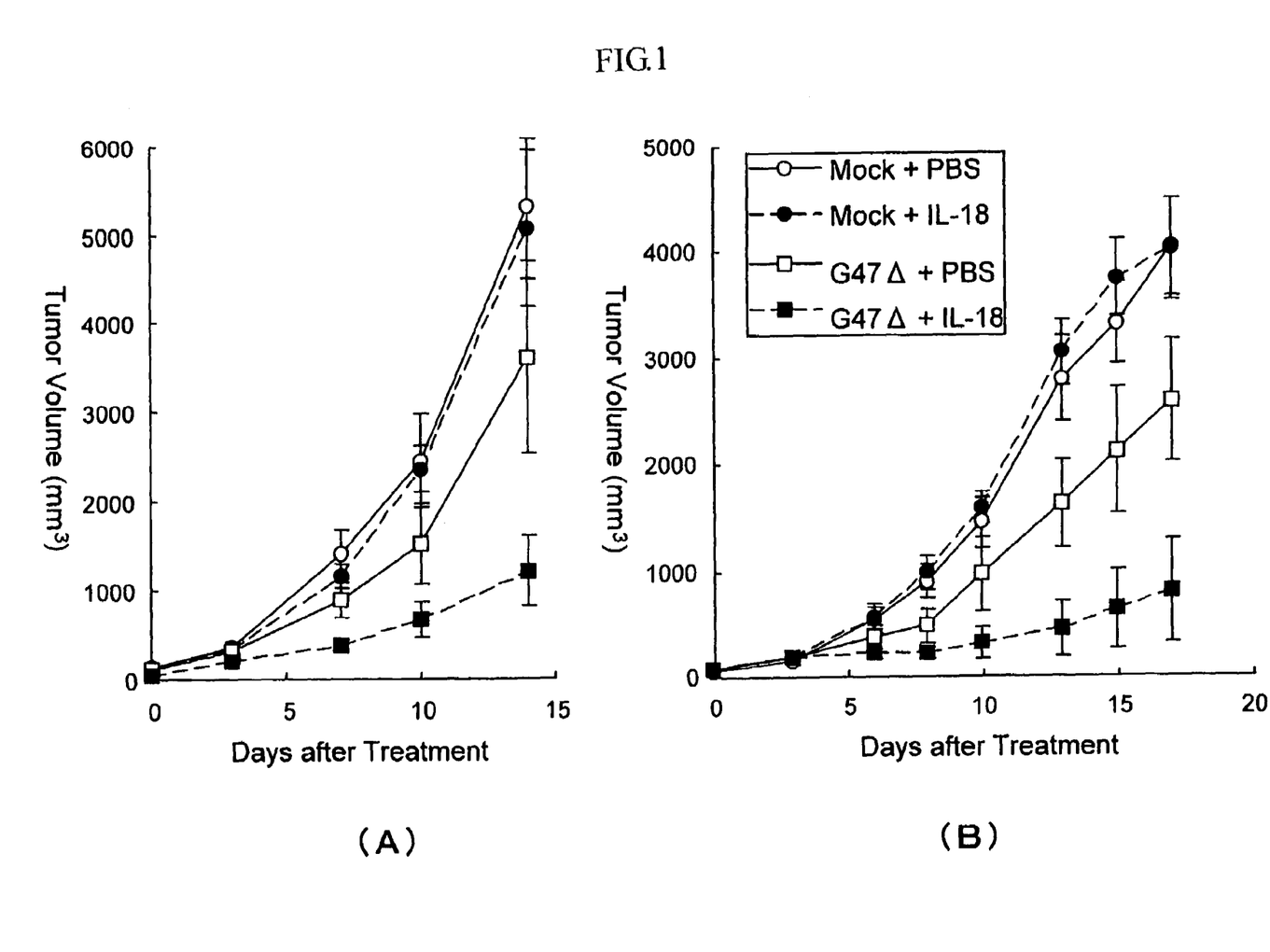
FIG. 1 shows the results of a test of the effects of the co-administration of G47Δ and IL-18 in mice having subcutaneous Neuro2a tumors.

Once the cancer tissue reached 5 to 6 mm in diameter, the model mice were divided into groups of 6 or 7 animals each. In the case of the two G47Δ-administered groups, G47Δ ($1 \times 10^6$ pfu) was administered twice by direct injection into the cancer tissue, on day 0 and day 3. In the case of the two groups that did not receive G47Δ (labeled as "mock" in the figure), phosphate buffered physiological saline (PBS) containing 10% glycerol was administered twice by direct injection into the cancer tissue, on day 0 and day 3.

IL-18 (1 µg/day) was injected intraperitoneally each day from day 0 to day 6 in one of the groups receiving G47Δ and in one of the groups that did not receive G47Δ, while PBS was injected intraperitoneally each day from day 0 to day 6 in the other group receiving G47Δ and in the other group that did not receive G47Δ. The tumor tissue was measured and its volume was determined by length×width×height (mm).

These experiments were carried out twice, and the results are shown in FIG. 1. In both experiments, the G47Δ-administered groups had a lower rate of cancer volume enlargement than did the groups not receiving G47Δ. In particular, the co-administration group (filled square) had a substantially lower growth rate than even the group receiving G47Δ alone (open square), thus confirming that co-administration caused an enhancement of the anticancer activity.

No differences were seen between the two groups that did not receive G47Δ (filled circle and open circle), which confirmed that an anticancer activity was not shown by the administration of 1 μg/day IL-18 alone.

Example 2

Induction of Antitumor Immunity by the Co-administration of IL-18 and G47Δ

Three animals each were removed on day 20 from the mice in the group receiving both G47Δ and IL-18, the group receiving G47Δ but not IL-18, the group receiving IL-18 but not G47Δ, and the group receiving neither G47Δ nor IL-18 in the test shown on the right in FIG. 1, and spleen cells were extracted from each mouse. The spleen cells ($2\times10^5$ in each case) were cultured both in the presence and in the absence of Neuro2a cells ($5\times10^5$) that had been pretreated with mitomycin C, for 24 hours in the IFN-γ production test and for 48 hours in the IL-4 production test. The number of IFN-γ-producing cells and the number of IL-4-producing cells were measured by ELISPOT assay.

Figure 2:
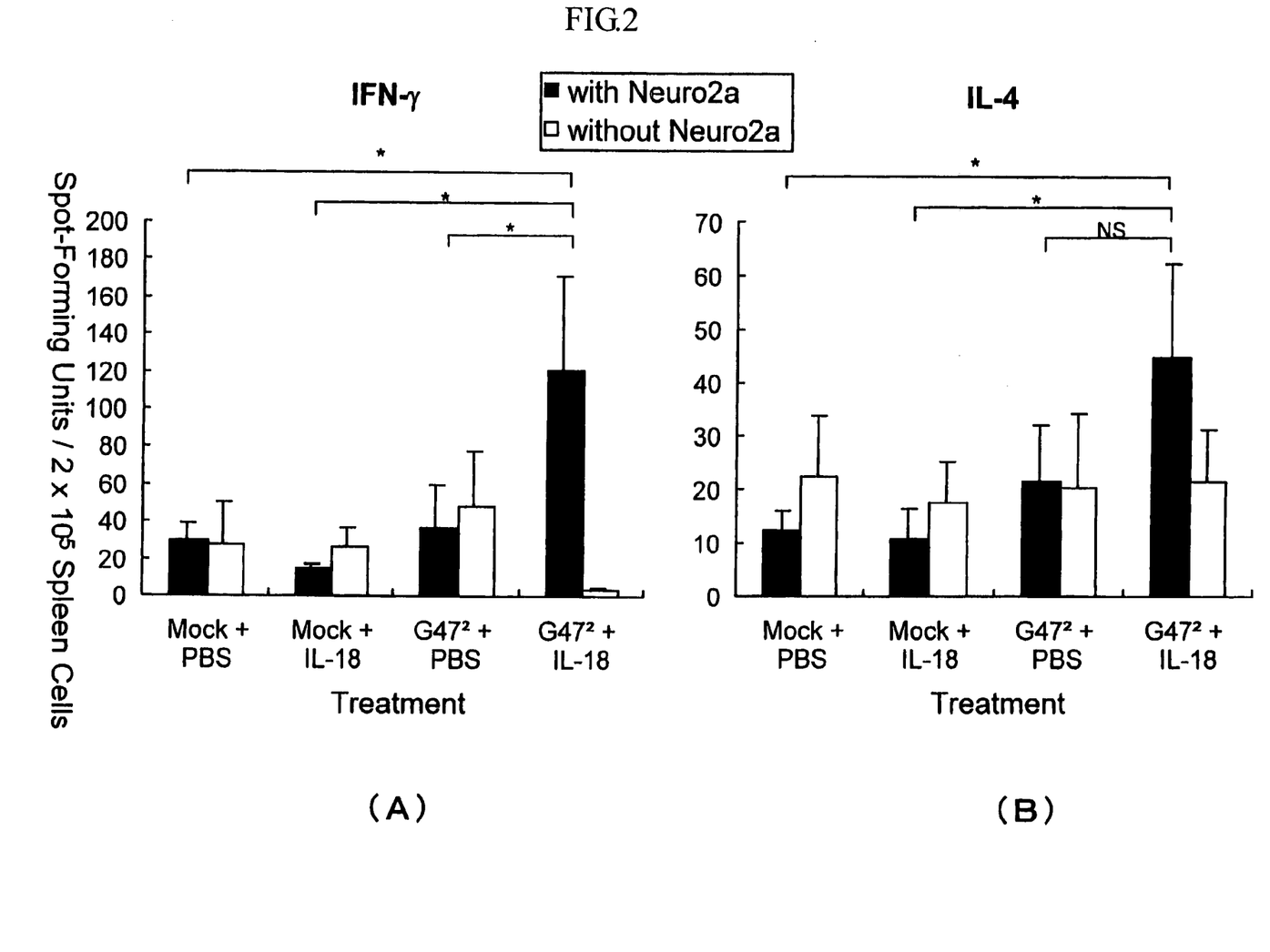
FIG. 2 shows the results of a test verifying the induction by G47Δ/IL-18 co-administration of spleen cells reactive to stimulation by tumor cells.

The results are shown in FIG. 2. IFN-γ-producing cells elicited by stimulation with Neuro2a cells were substantially increased in the G47Δ/IL-18 co-administration group in comparison to all other groups. With regard to IL-4-producing cells, the G47Δ/IL-18 co-administration group presented a significant increase over the two groups not receiving G47Δ, but was not significantly different from the group receiving G47Δ but not IL-18.

Example 3

Anticancer Effect of G47Δ/IL-18 Co-administration with Respect to Remote Tumor Tissue An enhancement of the induction of systemic antitumor immunity was confirmed for G47Δ/IL-18 co-administration. A/J mice were used that had subcutaneous Neuro2a tumor tissue (diameter about 4 mm) on both the right and left flanks. Each group contained 6 animals. In the groups receiving G47Δ, G47Δ ($2\times10^6$ pfu) was injected twice, on day 0 and day 3, only into the tumor tissue on the left side, and in the groups not receiving G47Δ, PBS containing 10% glycerol was injected twice, on day 0 and day 3, only into the tumor tissue on the left side.

In the groups receiving IL-18, IL-18 (1 μg/day) was injected intraperitoneally 7 times, from day 0 to day 6, while in the groups not receiving IL-18, PBS was injected 7 times from day 0 to day 6. The tumor tissue was measured and the volume was determined by length×width×height (mm).

Figure 3:
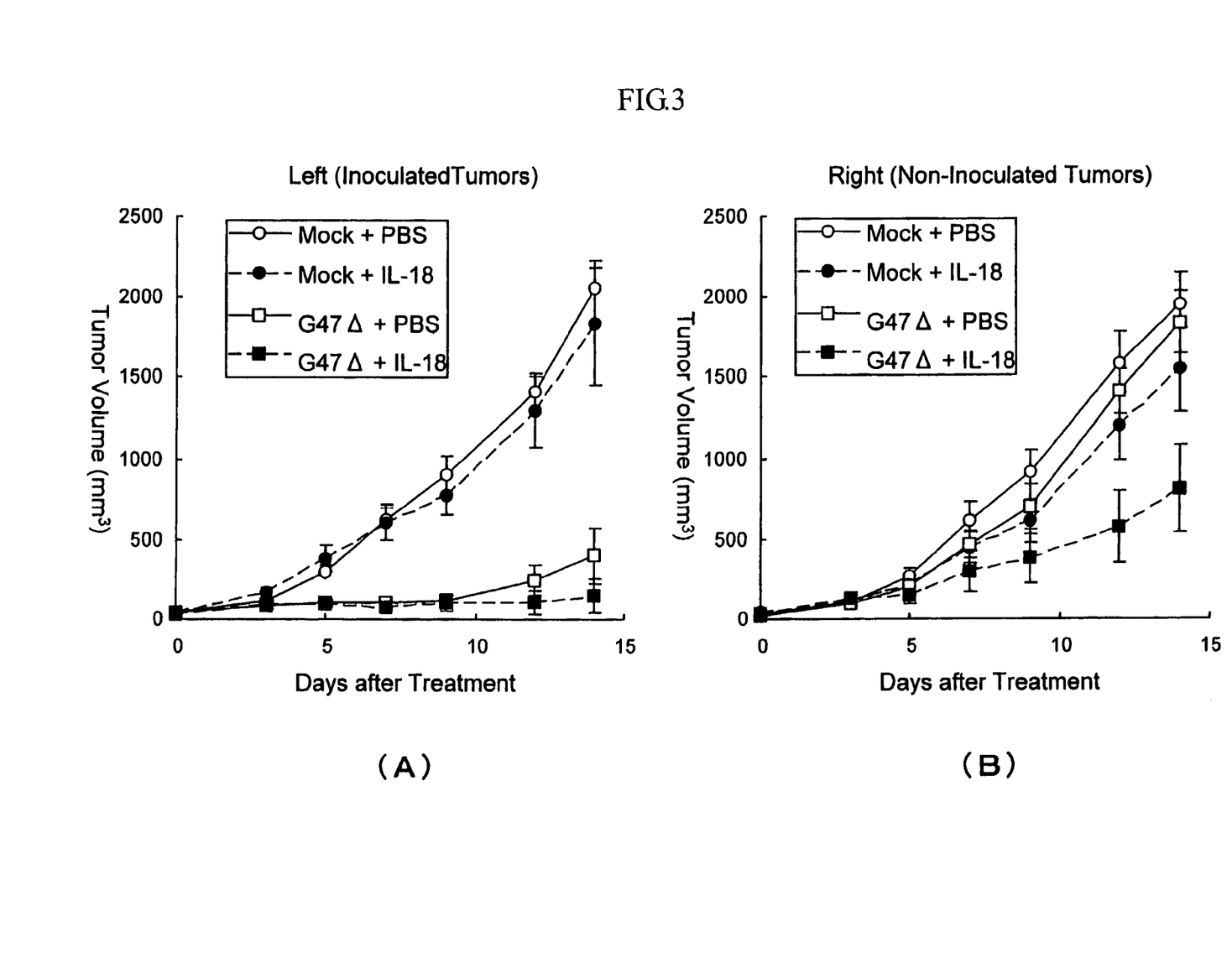
FIG. 3 shows the results of a test of the anticancer activity due to G47Δ/IL-18 co-administration on remote tumor tissue not inoculated with G47Δ.

The results are shown in FIG. 3. With regard to the increase in tumor volume on the right side, there was no significant difference between the group receiving only G47Δ (open square) and the groups not receiving G47Δ (open circle and filled circle); however, the increase in tumor volume was significantly retarded in the G47Δ/IL-18 co-administered group (filled square).

These results confirmed that, even when a systemic antitumor immunity is not seen for the administration of IL-18 alone or for the administration of G47Δ alone, a systemic antitumor immunity is induced by the co-administration of IL-18 and G47Δ at the same doses as for administration alone, thus confirming the appearance of an anticancer activity even in remote tumor tissue not inoculated with G47Δ.

Example 4

Effect of G47Δ/IL-18 Co-administration in Nude Mice

In this example, Neuro2a tumor cells were subcutaneously transplanted into nude mice (lacking T-lymphocytes). Four groups of 6 to 7 animals each were made up from animals in which the tumor tissue had reached a diameter of about 6 mm; the groups were a group receiving both G47Δ and IL-18, a group receiving G47Δ but not receiving IL-18, a group not receiving G47Δ but receiving IL-18, and a group receiving neither G47Δ nor IL-18. The dosage and administration protocol were the same as in Example 1.

Figure 4:
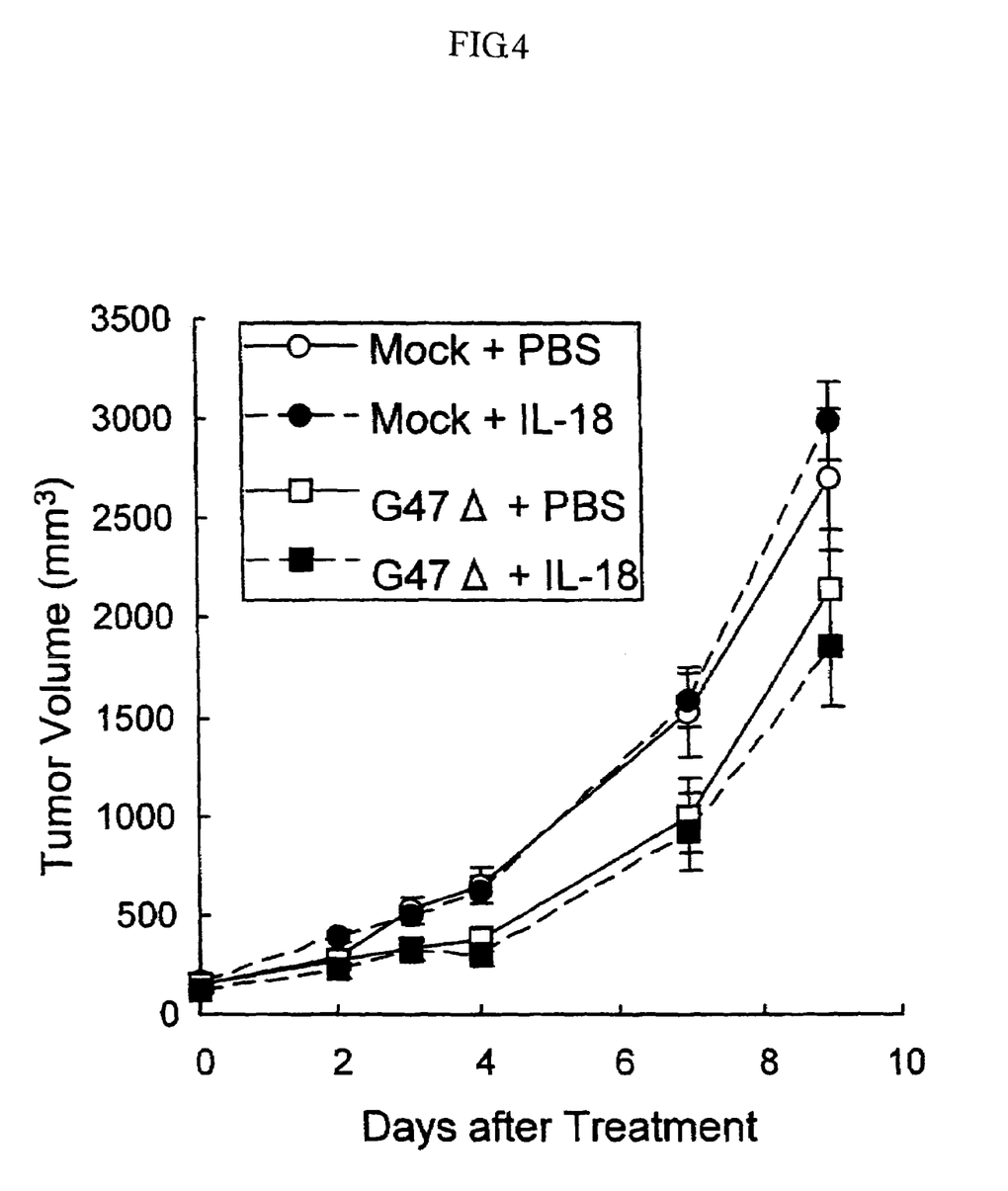
FIG. 4 shows the results of a test of the effect of the co-administration of G47Δ and IL-18 in nude mice.

The results are shown in FIG. 4. The increase in tumor volume was significantly inhibited in the two G47Δ-administered groups (open square and filled square) compared with the two groups that did not receive G47Δ (open circle and filled circle); however, a significant difference was not observed between the group receiving only G47Δ (open square) and the group receiving both G47Δ and IL-18 (filled square).

These results demonstrated that the enhancement in the anticancer activity of G47Δ caused by the co-administration of IL-18 requires the presence of T-lymphocytes and is due to an immune-mediated mechanism.

Example 5

Influence of IL-18 Administration on G47Δ Viral Replication in Cancer Tissue

G47Δ was injected on day 0 into the tumor tissue of A/J mice having a subcutaneous Neuro2a tumor with a diameter of about 6 mm. Among these mice, IL-18 (1 μg/day) was injected intraperitoneally 7 times in the group receiving IL-18, from day 0 to day 6, while PBS was injected intraperitoneally 7 times in the group not receiving IL-18, from day 0 to day 6. The subcutaneous tumor was removed, in each case from 3 mice, at 30 minutes, 2 days, 4 days, 7 days, and 11 days after G47Δ administration and the G47Δ titer in the tumor was measured by a plaque assay.

Figure 5:
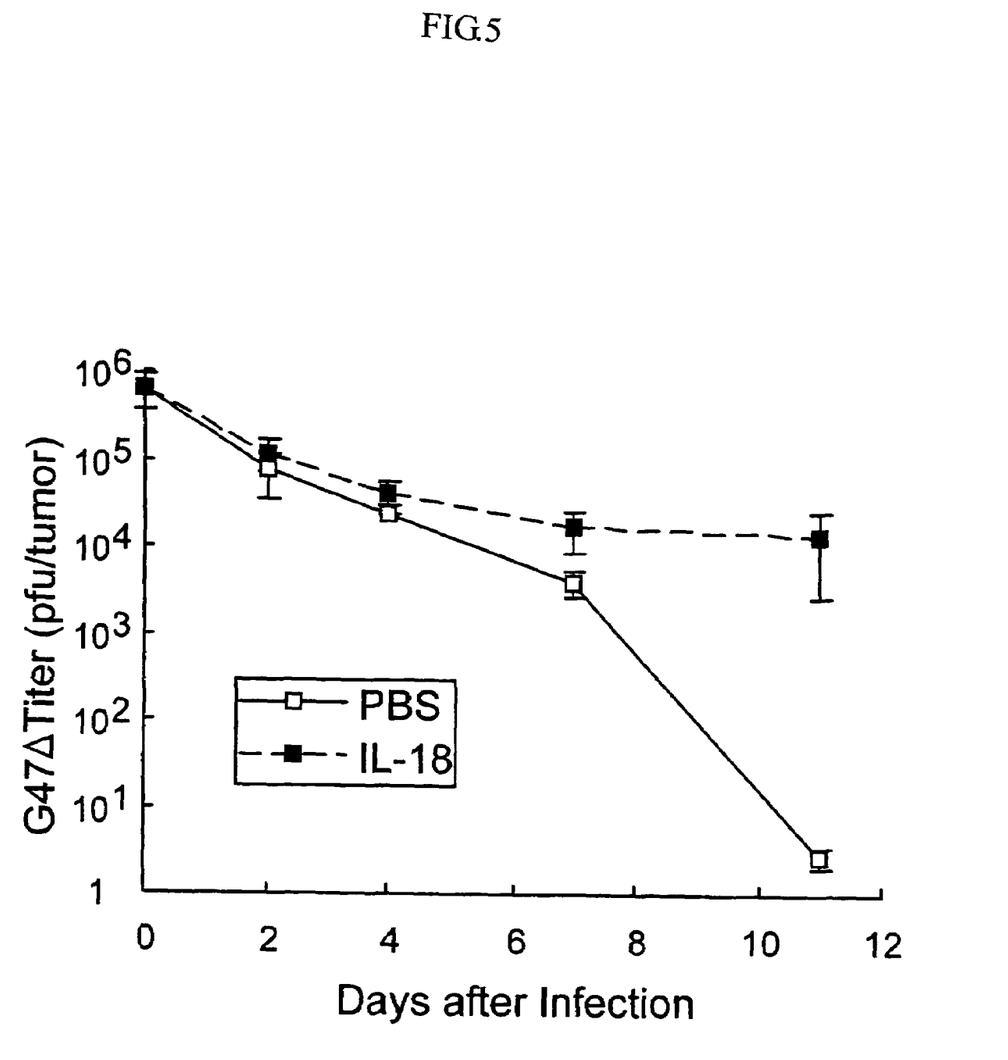
FIG. 5 shows the results of a test of the influence of the administration of IL-18 on viral replication by G47Δ within cancer tissue.

The results are shown in FIG. 5. A statistically significant difference in the detected titer of G47Δ from the tumor was not found at any time point between the group receiving IL-18 (filled square) and the group not receiving IL-18 (open square), and a significant difference in viral replication capacity was therefore not observed. This result was also reproduced in a separate experiment using the same protocol.

This result demonstrated that the enhancement of the anticancer activity of G47Δ by the co-administration of IL-18 does not have an influence on the viral replication capacity of G47Δ.

Example 6

Effect of G47Δ/IL-18 Co-administration in the Presence of Depletion of T-lymphocyte Subsets Using anti-CD4 antibody and anti-CD8 antibody, the CD4+ T-lymphocytes or CD8+ T-lymphocytes were depleted in A/J mice having subcutaneous Neuro2a tumors in order to investigate the contributions of these immune cells to the effect from the co-use of G47Δ and IL-18.

Figure 6:
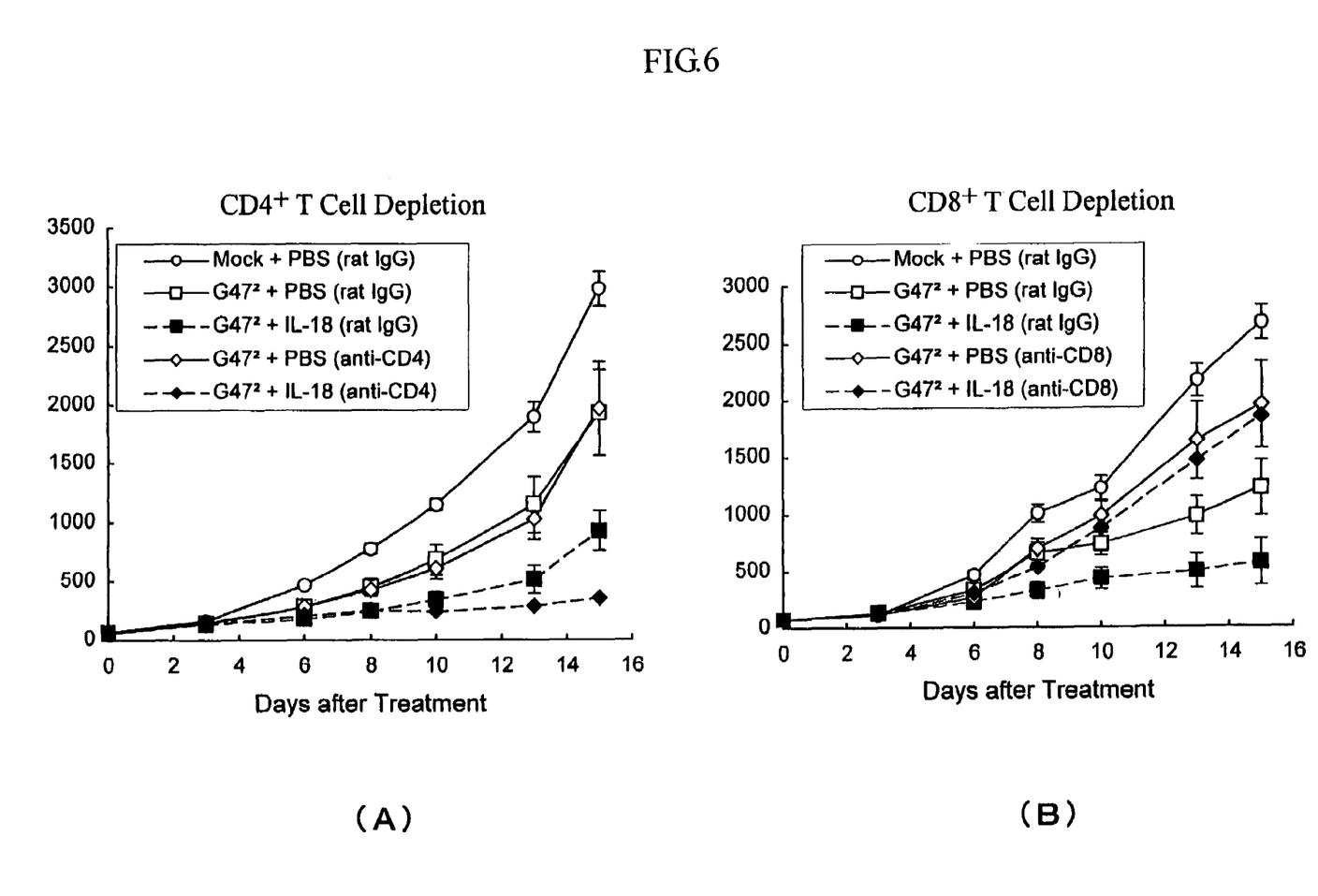
FIG. 6 shows the results of a test of the effect of the co-administration of G47Δ and IL-18 in the presence of the depletion of CD4+ T-lymphocytes or CD8+ T-lymphocytes.

A/J mice having subcutaneous Neuro2a tumor tissue (5 to 6 mm) were divided into groups of 6 to 7 animals each. In the case of the four G47Δ-administered groups, G47Δ ($2\times10^6$ pfu) was administered twice by direct injection into the cancer tissue, on day 0 and day 3. In the case of the single control group (labeled as "Mock+PBS" in the figure), phosphate buffered physiological saline (PBS) containing 10% glycerol was administered twice by direct injection into the cancer tissue, on day 0 and day 3.

IL-18 (1 µg/day) was injected intraperitoneally each day from day 0 to day 6 in half of the groups receiving G47Δ, while PBS was injected intraperitoneally each day from day 0 to day 6 in the other half.

In the CD4+ T-lymphocyte depletion test (diagram on the left), anti-CD4 antibody (250 µg) was administered intraperitoneally 1 day before and on day 2, 6, and 12 of G47Δ administration, in one of the two groups receiving both G47Δ and IL-18 and in one of the two groups receiving G47Δ but not IL-18. In the groups not receiving anti-CD4 antibody, rat IgG was administered as the control in the same amount and on the same schedule.

The CD8+ T-lymphocyte depletion test (diagram on the right) was carried out in the same manner as the CD4+ T-lymphocyte depletion test using anti-CD8 antibody (50 µg) rather than the anti-CD4 antibody.

The tumor tissue was measured and the volume was determined by length×width×height (mm).

The results are shown in FIG. 6. The enhancement in the anticancer activity of G47Δ due to the co-use of IL-18 was not influenced by depletion of CD4+ T-lymphocytes, but the anticancer activity enhancement caused by the co-use of IL-18 was extinguished when CD8+ T-lymphocyte depletion was carried out. This demonstrated that a mechanism requiring CD8+ T-lymphocytes participates in the effects due to the co-administration of IL-18.

Example 7

Effect of G47Δ/IL-18 Co-administration on Brain Tumors $5 \times 10^4$ Neuro2a cells were implanted intracerebrally in A/J mice. After five days had elapsed, G47Δ ($2 \times 10^5$ pfu) was administered by injection into the tumor tissue in the G47Δ-administered group, while PBS containing 10% glycerol was administered by injection into the tumor tissue in the group not receiving G47Δ. IL-18 (1 µg/day) was administered by intraperitoneal injection each day from G47Δ administration day 0 to day 6 in the group receiving IL-18, while PBS was administered by intraperitoneal injection each day from G47Δ administration day 0 to day 6 in the group not receiving IL-18. The survival times of the mice were measured.

Figure 7:
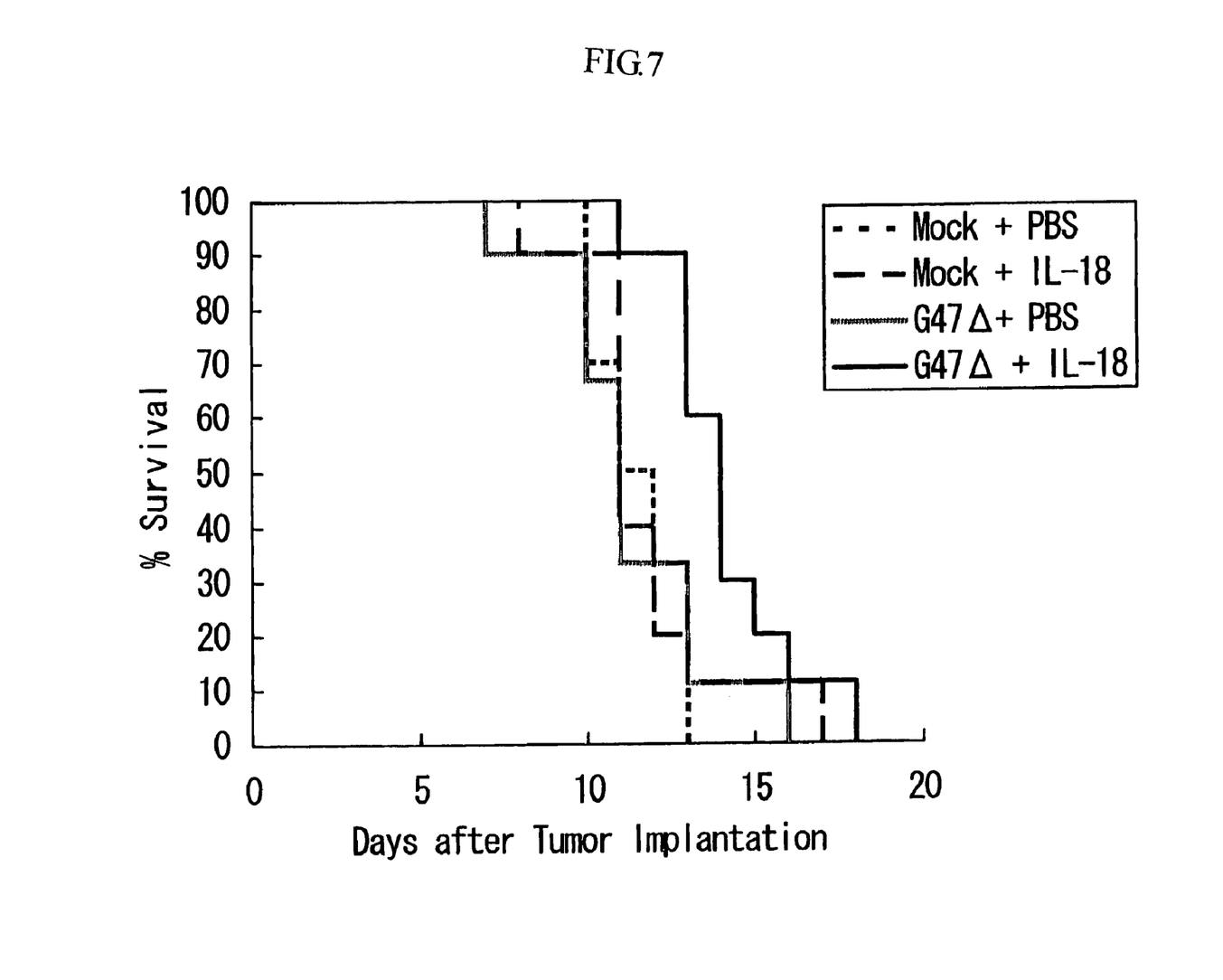
FIG. 7 shows the results of a test of the effects of the co-administration of G47Δ and IL-18 on brain tumors.

The results are shown in FIG. 7. The survival time of the G47Δ/IL-18 co-administration group was significantly lengthened in comparison to the other groups. This confirmed that the co-administration of IL-18 manifested a satisfactory anticancer activity enhancing effect even on an intracerebral tumor, where it is difficult for immune effects to appear.

Example 8

Enhancement of the Antitumor Activity of Recombinant HSV (Local Administration) and IL-18 (Systemic Administration), by the Local Administration of IL-12

An enhancement of antitumor activity and a systemic antitumor immunity-mediated enhancement of antitumor activity against remote tumors were then confirmed for the local administration of IL-12 in combination with the co-use of G47Δ (local administration) and IL-18 (systemic administration) as described in the preceding examples.

IL-12 was administered locally in this example by the administration of recombinant HSV prepared by the insertion of a gene encoding IL-12 into the viral genome of a recombinant HSV.

Figure 8:
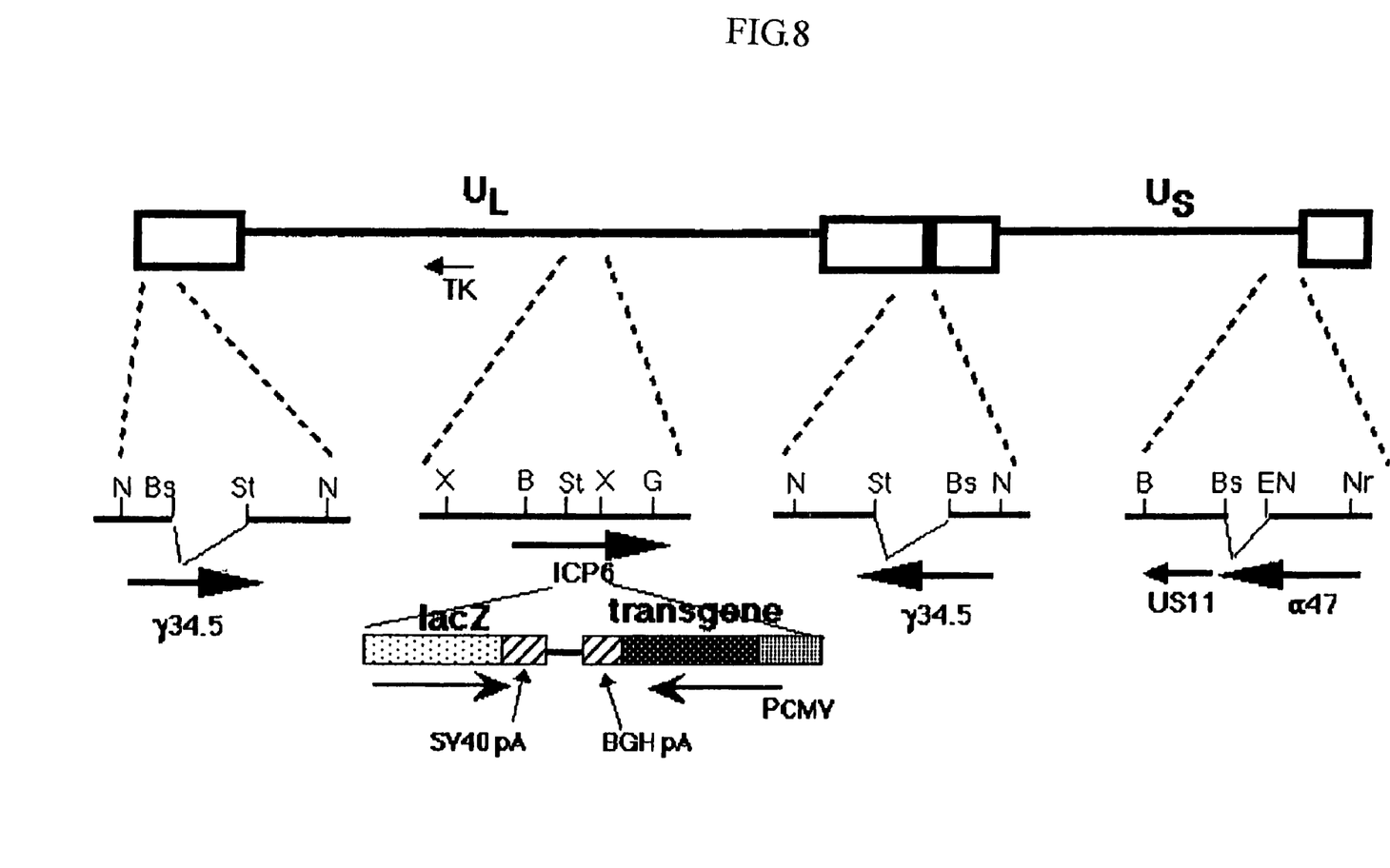
FIG. 8 shows the structure of T-mfIL 12, which is G47Δ viral DNA having an IL-12-encoding gene inserted therein as an expressible construct.

To obtain the local expression of IL-12, G47Δ viral DNA having an IL-12-encoding gene inserted as an expressible construct, as shown in FIG. 8, was first constructed (this IL-12-inserted G47Δ viral DNA is referred to as "T-mfIL 12" hereafter). In the figure, the boxes on the line are inverted repeat sequences that flank the unique $U_L$ and $U_S$ sequences in herpes viral DNA. As shown in the figure, T-mfIL 12 has a 1.0 kb deletion in both copies of γ34.5, a 312 bp deletion in the ICP47 site, and an 894 bp deletion between the ScaI-XhoI sites of the ICP6 gene. The mouse IL-12 gene (labeled as the "transgene" in the figure) and the LacZ gene were inserted in the ICP6 deletion site. The thick arrows in the figure refer to the direction of transcription. In addition, N refers to the NcoI restriction site; Bs refers to the BstEII restriction site; St refers to the StuI restriction site; X refers to the XhoI restriction site; B refers to the BamHI restriction site; Sc refers to the ScaI restriction site; G refers to the BglII restriction site; EN refers to the EcoNI restriction site; and Nr refers to the NruI restriction site.

Using A/J mice having subcutaneous Neuro2a tumor tissue approximately 5 mm in diameter on both the right and left flanks, T-mfIL 12 ($1 \times 10^6$ pfu, in PBS containing 10% glycerol) was injected twice in the T-mfIL 12-administered groups, on day 0 and day 3, only within the tumor tissue on the left side, while in the groups not receiving T-mfIL 12 only PBS containing 10% glycerol was injected twice, on day 0 and day 3, only within the tumor tissue on the left side (5 or 6 animals in each group).

On the other hand, IL-18 (1 µg/day) was intraperitoneally injected in the IL-18-administered groups 7 times from day 0 to day 0, while in the groups not receiving IL-18, PBS was intraperitoneally injected 7 times from day 0 to day 0. The tumor tissue was measured and the volume was determined by length×width×height (mm).

Figure 9:
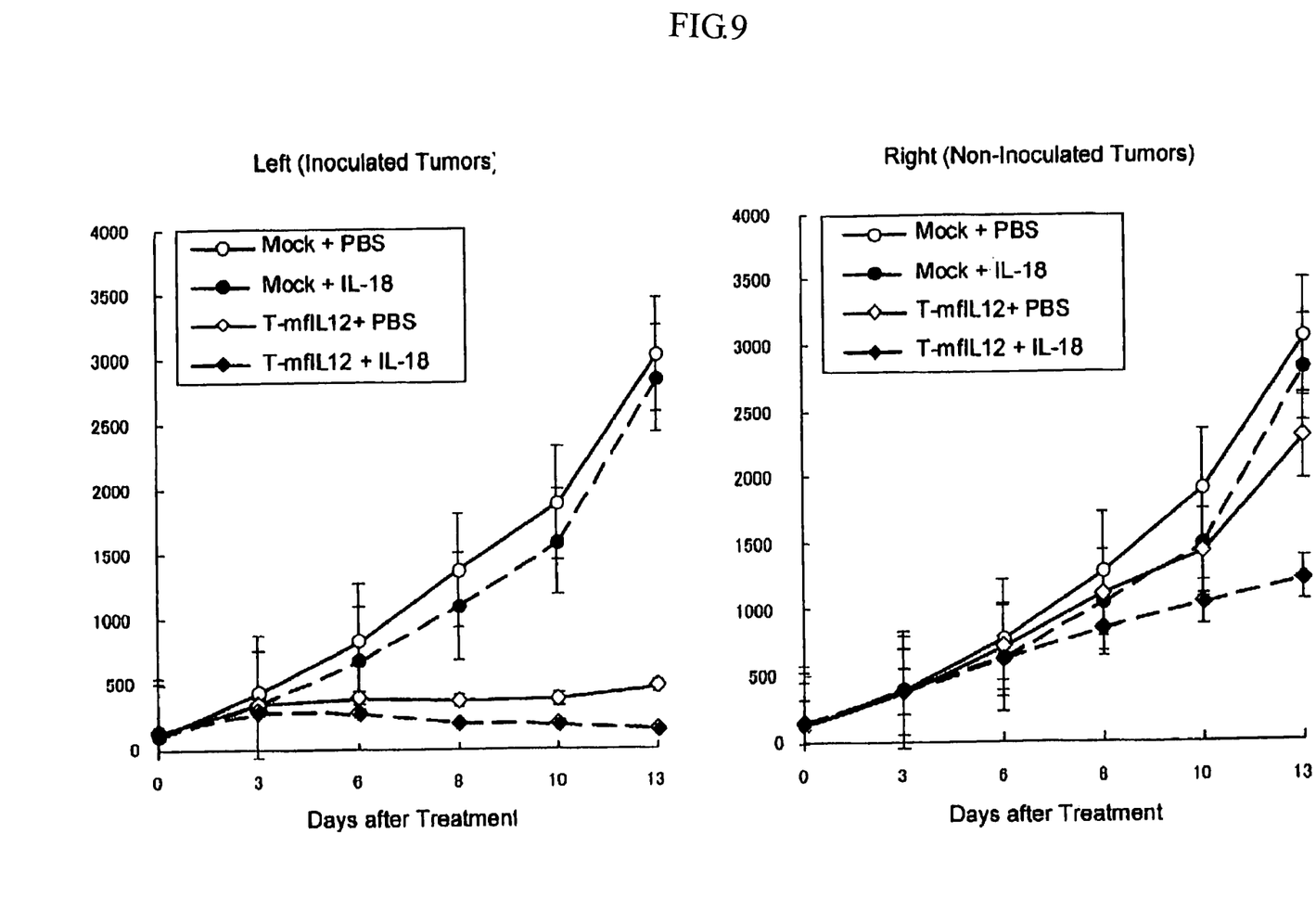
FIG. 9 shows the results of tests of the antitumor activity on tumors that have received a viral inoculation (left) and remote tumors (right), for the co-administration of IL-18 (systemic administration) and IL-12-expressing G47Δ (local administration to the left-side tumor), in mice having subcutaneous Neuro2a tumors on both sides.

The results are shown in FIG. 9. In the figure, "Mock+PBS" refers to groups that received neither T-mfIL 12 nor IL-18; "Mock+IL-18" refers to groups that did not receive virus, but in which IL-18 was administered systemically; "T-mfIL 12+PBS" refers to groups that did not receive IL-18, but which were administered IL-12-expressing recombinant HSV; and "T-mfIL 12+IL-18" refers to groups in which the local administration of IL-12-expressing recombinant HSV was combined with the systemic administration of IL-18.

With regard to the tumors on the left side, tumor enlargement was significantly inhibited even by the administration of T-mfIL 12 alone (open diamond) in comparison to the groups that did not receive the virus (open circle and closed circle), while an even more significantly strengthened antitumor activity was shown by the co-use of T-mfIL12 and IL-18 (filled diamond).

In addition, with regard to the remote, right-side tumors, only a modest inhibition of tumor enlargement was seen for the group receiving T-mfIL 12 alone (open diamond) in comparison to the groups that did not receive the virus, while the co-administration of IL-18 (filled diamond) resulted in a clearly enhanced antitumor activity, resulting in a significant difference with respect to the group receiving T-mfIL 12 alone.

These results demonstrated that, for both virus-inoculated tumors and non-inoculated remote tumors, the antitumor activity of recombinant HSV that incorporates the IL-12 gene is enhanced by the systemic co-administration of IL-18, even in those cases where tumor enlargement cannot be effectively inhibited by the systemic administration of IL-18 alone.

I claim:

1. A method of treating cancer comprising co-administration of interleukin 18 and a recombinant herpes simplex virus that selectively replicates in cancer cells, wherein said interleukin 18 is administered as a protein and wherein the γ34.5 gene, the ICP6 gene and the ICP47 gene of the recombinant herpes simplex virus have been deleted or inactivated.

2. The method according to claim 1, wherein the interleukin 18 is administered systemically.

3. The method according to claim 2, further comprising local administration of interleukin 12 at a tumor tissue.

4. The method according to claim 2, further comprising local administration at a tumor tissue of a recombinant herpes simplex virus that selectively replicates in cancer cells, wherein a gene coding for interleukin 12 has been inserted expressively in the genomic DNA of the recombinant herpes simplex virus.

5. The method according to claim 1, wherein the recombinant herpes simplex virus is injected into a tumor tissue.

6. The method according to claim 1, wherein the cancer is located separately from the tumor tissue injected with the herpes simplex virus.

7. A method according to claim 1 or 2, wherein said interleukin 18 is administered in an amount that is ineffective for interleukin 18 alone to treat cancer.

8. A method according to claim 1 or 2, wherein said interleukin 18 is administered at a dose sufficiently low to avoid toxicity.

9. A method of treating cancer, comprising administering a recombinant herpes simplex virus that selectively replicates in cancer cells into a tumor tissue and systemically administering interleukin 18 as a protein, wherein the γ34.5 gene, the ICP6 gene and the ICP47 gene of the recombinant herpes simplex virus have been deleted or inactivated, and a gene coding for interleukin 12 has been inserted expressively in the genomic DNA of the recombinant herpes simplex virus.

10. A method according to claim 9, wherein said interleukin 18 is administered in an amount that is ineffective for interleukin 18 alone to treat cancer.

11. A method according to claim 9, wherein said interleukin 18 is administered at a dose sufficiently low to avoid toxicity.

12. A method according to claims 1 or 9, wherein interleukin-18 is administered by injection in amount of 0.1 to 1000 µg/kg.

* * * * *

UNITED STATES PATENT AND TRADEMARK OFFICE
CERTIFICATE OF CORRECTION

| | | |
|---|---|---|
| PATENT NO. | : 7,655,459 B2 | |
| APPLICATION NO. | : 10/594964 | |
| DATED | : February 2, 2010 | |
| INVENTOR(S) | : Tomoki Todo | |

It is certified that error appears in the above-identified patent and that said Letters Patent is hereby corrected as shown below:

On the Title Page:

The first or sole Notice should read--

Subject to any disclaimer, the term of this patent is extended or adjusted under 35 U.S.C. 154(b) by 118 days.

Signed and Sealed this
Fifteenth Day of March, 2011

David J. Kappos
*Director of the United States Patent and Trademark Office*